(12) United States Patent
Epple et al.

(10) Patent No.: US 7,959,682 B2
(45) Date of Patent: Jun. 14, 2011

(54) METHOD FOR PRODUCING BONE SUBSTITUTION MATERIAL

(75) Inventors: Matthias Epple, Hattingen (DE); Drazen Tadic, Hamburg (DE)

(73) Assignee: ADC Advanced Dental Care GmbH & Co. KG, Obernburg (DE)

( * ) Notice: Subject to any disclaimer, the term of this patent is extended or adjusted under 35 U.S.C. 154(b) by 660 days.

(21) Appl. No.: 10/955,925

(22) Filed: Sep. 30, 2004

(65) Prior Publication Data

US 2005/0163861 A1    Jul. 28, 2005

(30) Foreign Application Priority Data

Sep. 30, 2003 (EP) .................................. 03021986

(51) Int. Cl.
*A61F 2/28* (2006.01)
(52) U.S. Cl. ............... 623/23.61; 623/23.56; 623/23.57; 623/901; 424/549
(58) Field of Classification Search .................. None
See application file for complete search history.

(56) References Cited

U.S. PATENT DOCUMENTS

| 6,302,913 B1 * | 10/2001 | Ripamonti et al. ........ 623/16.11 |
| 2003/0167093 A1 * | 9/2003 | Xu et al. .................... 623/23.56 |

FOREIGN PATENT DOCUMENTS

| FR | 2 744 020 | 8/1997 |
| WO | WO 02/065955 A1 | 8/2002 |
| WO | WO 02/010243 A1 | 12/2002 |
| WO | WO 03/057086 A2 | 7/2003 |

OTHER PUBLICATIONS

Lin et al, "Prepartion of Macroporous Biodegradable PLGA Scaffolds for Cell Attachment with the Use of Mixed Salts as Porogen Additives" Journal of Biomedical Material Research, 2002, vol. 63, No. 3, pp. 271-279.*
Ma et al, "Synthetic nano-fibrillar extracellular matrices with predesigned macroporous architectures" Journal of Biomedical Material Research (2000), vol. 52, pp. 430-438.*
Zhang et al, "Synthetic nano-fibrillar extracellular matrices with predesigned macroporous architectures" Journal of Biomedical and Material Research, 2000, vol. 52, pp. 430-438.*
A Synthetic Aragonite-Based Bioceramic: Influence of Process Parameters on Porosity and Compressive Strength, Lucas-Girot et al., Biomaterials 23 (2002) pp. 503-510, Elsevier Science Limited.
Influence of Porosity on the Mechanical Resistance of Hydroxyapatite Ceramics Under Compressive Stress, Le Huec et al., Biomaterials 16 (1995) 113-118, Elsevier Science Limited.
Self-Organization Mechanism in a Bone-Like Hydroxyapatite/collagen Nanocomposite Synthesized in Vitro and Its Biological Reaction in Vivo, Kikuchi et al., Biomaterials 22 (2001) 1705-1711, Elsevier Science Limited.

* cited by examiner

*Primary Examiner* — Allison M Ford
(74) *Attorney, Agent, or Firm* — Ohlandt, Greeley, Ruggiero & Perle, LLP

(57) ABSTRACT

In order to provide a bone substitution material which enables mechanical stability and long-term in-vivo biocompatibility which can also be used for guided bone healing, the invention provides a method comprising the steps of providing a starting material comprising a mixture of at least a skeleton substance (20) and at least one functional substance, and building up a skeleton from the skeleton substance, thereby producing a profiled body (30), as well as a profiled body (30) containing a skeleton substance (20) and comprising a porous structure (10) with pores (12, 15) being interconnected with each other.

22 Claims, 11 Drawing Sheets

4A
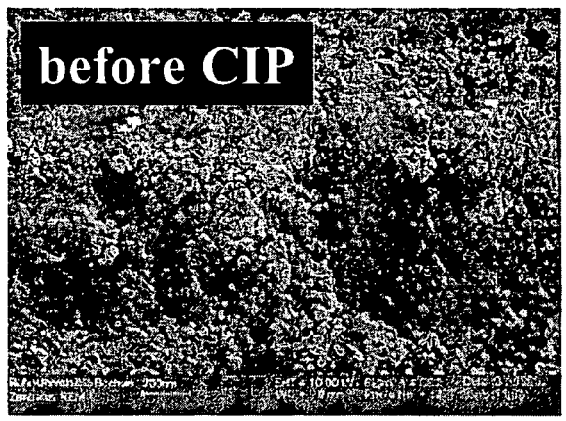
4B
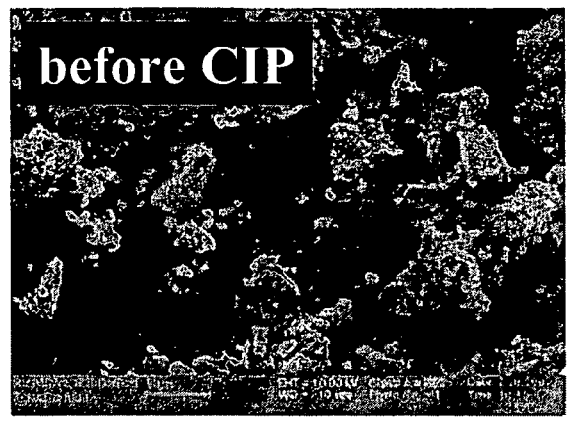
4C
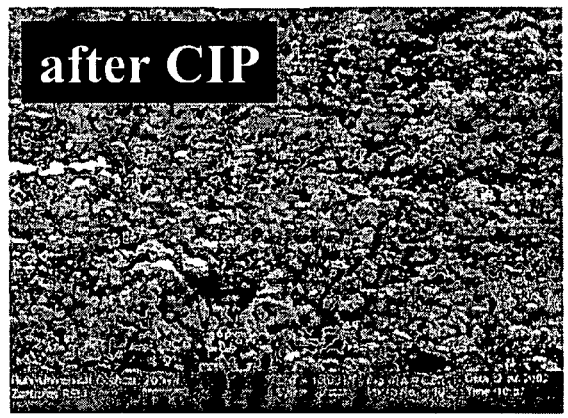
4D
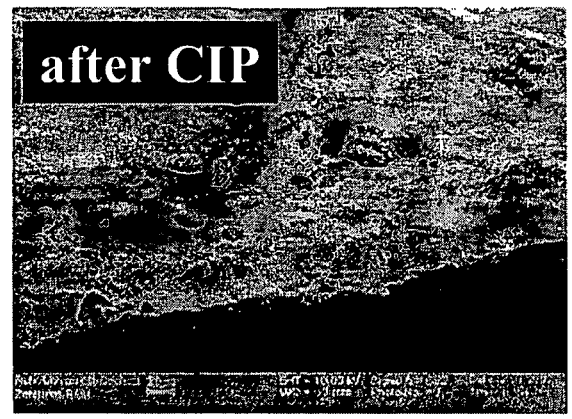
Figure 4

| Cold-isostatically pressed carbonated apatites (this work; cylinders; height/diameter in mm) | Method of preparation | Compressive strength / MPa | Young's modulus / GPa |
|---|---|---|---|
| 13 / 20 | uniaxial hot pressing (4 kbar, 240°C) | 5..6 | 1.2..2.6 |
| 32 / 16 | cold isostatic pressing (4 kbar, 25°C) | 21.8 | 1.6 |
| 16 / 16 | cold isostatic pressing (4 kbar, 25°C) | 26.1 | 1.3 |
| 8 / 8 | cold isostatic pressing (4 kbar, 25°C) | 47.6 | 2.2 |
| 8 / 4 | cold isostatic pressing (4 kbar, 25°C) | 25.6 | 1.1 |
| 4 / 4 | cold isostatic pressing (4 kbar, 25°C) | 27.5 | 0.8 |
| Selected biominerals | | | |
| Particles of bone (1) | morsellized to 2.1±1.3 mm diameter | - | 0.085-0.135 |
| Trabecular bone (2) | (measured by nanoindentation) | - | 11.4±5.6 |
| Compact human bone (3) | - | 133-193 | 11.5-27 |
| Diaphyseal cortical bone (2) | (measured by nanoindentation) | - | 20.1±5.4 |
| Dentine (3) | - | 250-350 | 11-17 |
| Enamel (3) | - | 95-370 | 9-84 |
| Selected biomaterials | | | |
| Macroporous HAP with 40 % porosity (4) | sintered at 1350°C | 30±8 | 1.4±0.4 |
| Microporous HAP with 22 % porosity (5) | pressing, followed by sintering above 1000°C | 348 | - |
| TCP-HA composites without porosity (1) | 3-5 mm diameter | - | 0.442-0.525 |
| Monoliths of calcium-deficient hydroxyapatite (CDHA) (6) | pressed at 38°C and 0.8 kbar after mixing with 11-20 wt% water | 84-172 | 5.97-7.31 |
| Monoliths of carbonated apatite (6) | pressed at 38°C and 0.8 kbar after mixing with 11-20 wt% water | 53-80 | 4.58-5.59 |
| HAP with 0.06 % porosity (7) | uniaxial pressing, slip casting and starch consolidation | - | 84 |
| Dense HAP ceramics (3) | - | 120-900 | 35-120 |

Figure 5

METHOD FOR PRODUCING BONE SUBSTITUTION MATERIAL

CROSS-REFERENCE TO RELATED APPLICATIONS

The present application is a nonprovisional application filed under 35 U.S.C. 111(a), which claims priority under 35U.S.C. 119(a)-(d) to European Patent Application No. 03021986.9, filed Sep. 30, 2003.

BACKGROUND OF THE INVENTION

1. Field of the Invention

The invention relates to a method for producing bone substitution material and a profiled body, which can in particular be produced using this method.

2. Description of the Related Art

Bone fractures and damage are serious health problems in all day clinical work. Common bone substitution materials are autografts, allografts, xenografts and various synthetic materials like polymers, metallic materials, composites and bioceramics. However, none of these materials provides a perfect solution in particular for guided bone healing because there always remain questions about mechanical stability, long-term in-vivo biocompatibility, and biodegradability.

Autograft sources, which are transplanted bone, for example from the iliac crest, show an excellent osteoinductivity—that means build-up of new bones by differentiation of osteogenic cells from less differentiated precursor cells—but they are not available in unlimited amounts and also require a secondary operation. In the case of allografts, that means a graft from one member of a species to a genetically different member of the same species, or xenografts, that means a graft from one member of a species to a member of a different species, there are concerns about a possible contamination with infectious material, such as, for example HIV, hepatitis or BSE).

Due to these reasons, there is an ongoing interest in synthetic sources for bone grafts because they can be highly biocompatible, nontoxic, biodegrabable, cause no immunological or irritating response, have excellent osteoconductivity and can be optimised for many specific applications. The term "osteoconductivity" refers to the growth of osteoblasts along a bone graft, that means build-up of real new bone tissue.

At the moment, the most prominent bone substitution materials are sintered calcium phosphate ceramics on the basis of hydroxyapatite (HAP; $Ca_5(PO_4)_3OH$) or $\beta$-tricalcium phosphate ($\beta$-TCP; $Ca_3(PO_4)_2$) and mixtures of both, the so-called biphasic calcium phosphates; BCP. Their chemical composition is related to that of natural bone mineral which is a calcium-deficient carbonated hydroxyapatite, leading to a good biocompatibility in bone contact. The main difference between sintered hydroxyapatite and bone mineral is the higher crystallinity and the absence of carbonate of the former.

The mineral component of bone is a so-called "biological apatite" in which carbonate in an amount of about 3 to 5 percent by weight substitutes phosphate ions, and which also contains small amounts of other ions. In the following the term "percent by weight is abbreviated with "wt.-%".

In addition, all biologically formed apatites in bone, dentin and mineralised tendons are nanocrystalline with enamel being the only exception. In terms of composition, bone mineral is only roughly comparable to sintered hydroxyapatite, due to the differences in carbonate content and particle size that influence the solubility.

This results in sintered hydroxyapatite having a much lower rate of biodegradation compared to the nanocrystalline bone mineral. If an acceptable lifetime in the body of about 2 to 5 years is desired, sintered hydroxyapatite ceramics are therefore not acceptable. The $\beta$3-TCP ceramics have a higher rate of biodegradation, but they have a different chemical composition than bone mineral.

If the biological performance of different bioceramics is compared, it must be noted that the biological incorporation of a bone graft is a physiological process controlled by the cells of the surrounding host bone, in particular osteoblasts and osteoclasts. This biochemical response is influenced by the geometry, the chemical composition and the morphological and mechanical properties of a given biomaterial.

Besides the problems of the biological incorporation of a bone graft related to bone fractures and damage, bone infections still represent a major problem in medicine. The main reason is the poor accessibility of the infected bone site by systemically administered antibiotics. Therefore, a local therapy is desired. It can be achieved by a suitable carrier for a controlled drug delivery system. A bone graft provides one possibility to realise such a carrier.

Currently, local treatments are mainly handled by implanting poly(methyl methacrylate) (PMMA) systems loaded with antibiotics into the infection site, for example as bone cements. However, PMMA implants are not biodegradable and either have to be removed after the healing process or remain in the implantation site like bone cements for the fixation of endoprostheses.

Thus, a resorbable biomaterial, allowing release of controlled amounts of an antibiotic ingredient with no second surgical procedure to remove it, would be advantageous, especially as bone substitution material.

Synthetic biomaterials have been used successfully in clinical applications as an alternative to autogeneous, xenogeneous and allogeneous bone graft materials. In case of ceramic materials like, for instance, calcium phosphate, the conventional ceramic manufacturing process involves the consolidation of powders by molding and sintering. Because high temperatures are involved in sintering processes, any active ingredient like a drug can only be added to the final implant.

Clinical practice further demands that a bone graft material is resorbed or dissolved within a reasonable time, that means that the implant is finally replaced by new bone tissue. This is not the case for sintered ceramics as they have a much lower solubility than the nanocrystalline carbonated bone mineral that is dissolved by osteoclasts. From the clinical point of view, the goal is a full integration of a bone graft into the dynamic human organism where bone is continuously dissolved and produced by remodelling. A further aim is to prepare biodegradable, mechanically stable implants which also contain bioactive compounds.

With respect to the implant itself, it should be noted that while a compact synthetic bioceramic shows good mechanical properties, only the surface of ceramic will be in contact with tissue. Usually there will be no ingrowth of bone but only a degradation starting from the surface. Consequently, compact materials achieve only a geometrical fixation.

However, while porous materials provide a mechanical interlock caused by ingrowth of bone tissue into the pores. Due to this reason, porous bioceramics are preferred in clinical practice.

In recent years, particular attention was paid to the synthesis of bioceramics with porous morphology to allow the ingrowth of bone tissue which further improves the mechanical fixation of the implant at the implantation site. If an implanted porous ceramic is progressively replaced by natural bone, its biomechanical properties more and more resemble those of natural bone. To introduce porosity into a ceramic object, various methods were developed.

The current methods to introduce porosity into a ceramic are mainly based on the admixture of a combustible organic material, like, for instance, a polymer, that burns away during firing, or on a water soluble salt that leaves free spaces in the resulting object after washing with water.

The first method allows to manufacture an interconnected pore system when polymer fibres are used. However, it requires high-temperature treatment, that means it leads to a highly crystalline, sintered ceramic material with a low rate of biodegradation.

A characteristic of this method is the potential for a wide variation of porosity and pore size by using different kinds of, in particular polymer, fibres as templates which act as porogens within the ceramic. The term "porogen" is used for a substance which acts as a spacer at locations where a pore is situated in the final product. However, to remove these organic templates, calcination is required which induces high-temperature processes.

Secondly, the salt-leaching method does not require annealing, but it usually leads to closed pores which do not form an interconnecting, natural bone-like pore network. Ma et al. described in their publication "Synthetic nano-fibrillar extracellular matrices with predesigned macropoporous architectures", J. Biomed. Mater. Res. (2000), pages 430 to 438, for example, that they used sugar fibres and porous sugar disks as water-soluble porogens for poly-L-lactide. A porosity caused by pores being interconnected to each other, a so-called "interconnecting porosity", was obtained; however, the porogens had to be oriented manually; a process that is not suitable for large-scale up-scaling.

However, there is no method available to produce materials with interconnecting porosity without sintering, except for mechanical hole-drilling. Thus, up to now it is in particular not possible to prepare an object with interconnecting pores of nanocrystalline, bone-mineral-like apatite because it would recrystallize during sintering.

SUMMARY OF THE INVENTION

Therefore, an objective of the invention is to provide a bone substitution material, in particular formed as a profiled body, which enables mechanical stability and long-term in-vivo biocompatibility.

In particular, it can be a further objective of the invention to provide a bone substitution material which is biodegradable.

It is a further objective of the invention to provide a bone substitution material which can be used for guided bone healing. Another objective of the invention is to provide a possibility for a resorbable biomaterial, allowing release of controlled amounts of an active ingredient. It is yet another objective of the invention to provide a bone substitution material with no second surgical procedure to remove it.

It is a further objective of the invention to provide a bone substitution material that can be made available in unlimited amounts.

DESCRIPTION OF THE PREFERRED EMBODIMENT

The invention provides a surprisingly simple solution referring to the above mentioned objectives already by a method according to claim 1. In addition, the invention provides a further solution by a profiled body according to claim 16. Further advantageous embodiments are subjects of the respective dependent claims.

The invention provides a method for producing bone substitution material, comprising the steps of providing a starting material comprising a mixture of at least one skeleton substance and at least one functional substance, and building up a skeleton from the skeleton substance, thereby producing a profiled body.

The method provides the production of a bone substitution material which has a high mechanical stability due to its skeleton. Because the invention enables choosing of the first substance, a long-term in-vivo biocompatibility can easily be realised as well as a biodegradable bone substitution material.

By choosing a respective functional substance, a bone substitution material is provided which can be used for guided bone healing.

As in particular chemical composition, crystallinity, geometry, and porosity of the bone substitution material can be adjusted by the preparation process, the biological requirements for different applications (orthopaedic surgery, maxillofacial surgery) can be met by choice of the appropriate material.

It is further possible to produce a profiled body comprising a resorbable biomaterial, allowing release of controlled amounts of an active ingredient. In particular, no second surgical procedure is necessary to remove the bone substitution material. In addition, the bone substitution material can be made available in unlimited amounts.

In particular, the functional substance can be embedded within the skeleton in order to provide the advantage of a homogeneous structure of the bone substitution material. Thus, constant properties across the entire bone substitution material can be achieved.

Further, according to the method of the invention, the profiled body can be prepared by cold-isostatic pressing to provide a bone substitution material with a high mechanical stability whithout the need of a high-temperature process like conventional sintering. The bone substitution material prepared by cold-isostatic pressing has a stability under the conditions of osteoclast attack which is much higher than that of sintered ceramics.

While the profiled bodies have a high mechanical stability, their chemical and crystallographic properties remain unchanged.

By a continuous crystallisation method, it is for example possible to prepare bone-mineral like calcium phosphates with nanocrystallinity and a carbonate content as in bone mineral in unlimited amounts with reproducible properties. By cold isostatic pressing, the precipitated powders can be processed into objects of a desired shape with considerable mechanical strength. Crystallinity and composition of the material are not affected by this processing step. This offers the possibility to prepare biomimetic materials for optimal bone substitution.

As a functional substance, at least one porogen can be added. Thus, the invention provides the advantage of being able to choose the kind and amount of at least one porogen, hence, to tailor the desired porous structure.

The method according to the invention can comprise the further step of washing out the at least one porogen using a solvent in order to produce a porous profiled body. By washing out at least one porogen, calcination, and, hence, thermal stress can advantageously be avoided. In particular, depending on the solubility of the porogen, water can be used as a solvent. In this case, advantageously any residual matter of the solvent remaining at the bone substitution material is harmless providing for example the possibility of avoiding expensive and time-consuming further clearing steps.

The method according to the invention can further comprise the additional step of preparing holes in the bone substitution material, in particular by machining.

Further shaping by, for instance, cutting and drilling, leads to macroporous implants or geometrically designed implants to meet individual implantation sites. In particular, such porous objects are suitable for bone tissue ingrowth. Advantageously, such materials as biomimetic bone substitution materials can be easier resorbed during bone formation in the defect than sintered ceramics.

In addition, the method according to the invention can comprise the further step of providing the profiled body with an active ingredient, in particular by dip-coating the profiled body into a solution of the active ingredient.

By providing the profiled body with an active ingredient, it is possible to use the bone substitution material as a drug carrier. In particular, an antibiotic substance can be provided right onto the profiled body, hence, infections can advantageously be treated at the location of their appearance. In particular, dip-coating is a method of easily providing a body with a layer of active ingredient. Advantageously, an easy method to produce a drug-loaded implant that could reduce infections in bones is provided. By changing the concentration of the drug solution the amount of, for instance, antibiotic within the bone substitution material can be adjusted.

However, in order to enhance the long-term release, it is advantageous to incorporate an active ingredient into the bone substitution material. Therefore, the invention also provides a method wherein at least one active ingredient is added as functional substance. By doing so, the active ingredient is a component of the material building-up the profiled body. Thus, a given amount of active ingredient per mass of profiled body is distributed over the whole volume of the profiled body resulting in a moderate concentration. Therefore, the driving force for diffusion of the active ingredient is lowered compared to dip-coating, hence, the total amount of active ingredient is released over a longer period of time.

There are several methods to apply the active ingredient besides dip-coating. First, the active ingredient can be provided by impregnating the first substance with the active ingredient. Impregnation is an advantageously easy method to produce a drug-loaded implant providing the possibility of changing the concentration of the drug solution, and, hence, the amount of drug within the bone substitution material.

To do so, only the solution containing the active ingredient has to be adjusted; production of the profiled body is independent thereof. In particular, profiled bodies can be produced in large numbers, whereby application of an active ingredient can be carried out fine-tuned in a further processing step which is adopted to the respective requirements.

Further, the active ingredient can be provided by co-precipitating the first substance with the active ingredient. By doing so, the active ingredient is advantageously homogeneous distributed in the first substance which will be the skeleton material of the bone substitution material. Therefore, a very homogeneous distribution of active ingredient within the profiled body is provided causing a substantially constant concentration of active agent across the profiled body. This in turn causes advantageously constant long-term release of the active ingredient.

For example, as the presented method allows to load a mechanically stable, biodegradable, nanocrystalline calcium phosphate with any soluble drug, this method opens new ways in the combination of bone substitution materials with bioactive compounds. For instance, materials can be provided for the treatment of osteomyelitis.

The method according to the invention can be advantageously carried out using different kinds of materials depending on the respective requirements. In particular, the first substance can comprise a polymer.

For example, the following polymers could be used: poly (L-lactide) (PLA), poly(glycolide) (PGA), poly(DL-lactide) (PDLLA), poly(dioxanone) (PDO), poly(DL-lactide-co-L-lactide) (PDLLLA), poly(glycolide-co-trimethylene carbonate) (PGA-TMC), poly(L-lactide-co-glycolide) (PGLLA), poly(β-hydroxybutyrate) (PHB), poly(DL-lactide-co-ε-caprolactone), poly(β-hydroxybutyrate-co-β-hydroxyvalerate), and poly(ε-caprolactone) (PCL).

Biodegradable polymers provide the advantage that an implant prepared from a biodegradable polymer can be engineered to degrade at a rate that will slowly transfer load to the healing bone. In order to be degradable, the materials have to contain bonds which are broken under physiological conditions. In particular, it is advantageous if the polymers contain bonds being hydrolytically clearable, because the degradation rate is independent from the location as water is available everywhere in tissue.

In addition, also the use of the following polymers is within the scope of the invention: polyethylene (PE), polypropylene (PP), polyethyleneterephtalate (PET), polyvinyl chloride (PVC), polycarbonate (PC), polyamide (PA), polytetrafluoro ethylene (PTFE), polymethylmethacrylate (PMMA), polyetheretherketone (PEEK), and polysulfone (PSU).

Further, the at least first substance can comprise a ceramics material. Referring to ceramics, crystallinity and particle size advantageously provide parameters to adopt the solubility of the material during the resorption by osteoclasts.

In particular, the ceramic material can comprise calcium phosphate. The in-vivo behaviour of calcium phosphate can be adjusted by formulation of the composition and structure of calcium phosphate. Various calcium phosphates being available are described in the publication "calcium orthophosphates in medicine: from ceramics to calcium phosphate cements" by M. Bohner, Injury (2000), pages S-D37 to S-D47 which is fully incorporated herein by reference.

Further, according to the invention the first substance can be conditioned to a powder comprising particles having diameters typically in the range of 250 μm to 400 μm. By doing so, the starting material provides a suitable so-called microporosity of the profiled body prepared out of the particles.

In order to tailor the macroporous structure of the profiled body, a polymer, in particular a water-soluble polymer can be used as a porogen. Due to their longitudinal shape, polymers are a suitable material to be a spacer for long, stretched-out pores.

The porogen can advantageously have a diameter in the range of 150 μm to 200 μm, in particular 170 μm. Providing of pores with a particular diameter and, thus, connectivity is important because the presence of a pore size of at least 150 μm is an essential requirement for osteoconduction.

Furthermore, the porogen can have a length in the range of 5 mm to 10 mm. While being small enough to be easily mixable with the first substance, porogens of this dimensions at the same time have a sufficient length to provide long pores inside the bone substitution material.

For example, the polymer can be poly-vinyl alcohol (PVA), which is available in the desired size range and additionally is in water soluble.

In order not only to provide for a pore structure comprising long stretched-out pores, but also chamber-like pores, a substance comprising particles is used as a porogen.

The particles used as porogens typically have mean diameters in the range of 250 μm to 400 μm. The term "mean diameter" refers to an average diameter of the collective of particles.

In particular, salt crystals and water-soluble polymer fibres as porogens can be mixed with calcium phosphate powder, followed by cold-isostatic pressing. As both porogens are easily water soluble, they can be removed without the need to sintering. Larger pores are formed by the salt crystals and polymer fibres from bridging channels between these pores.

The use of salt crystals and fibres of a water-soluble polymer as porogens allows to prepare objects with macroscopic interconnecting porosity that could be used as bone substitution materials that permit the ingrowth of bone.

Advantageously, the method according to the invention is applicable to all kinds of water-insoluble materials that can be compacted without sintering.

According to the invention, cold isostatic pressing is typically carried out at a pressure of 200 MPa to 600 MPa. Already with this low value of pressure, stable profiled bodies can produced. Hence, energy consumption is advantageously low.

Further, the method according to the invention is carried out at moderate temperatures. Thus, the probability for any thermal damage of any substance is extremely low. In particular, cold isostatic pressing can be carried out around ambient temperature at a temperature in the range of 15° C. to 35° C.

The method according to the invention further provides washing out the at least one porogen to be carried out at a temperature $\theta_A$ with $\theta_A \geq \theta_{S,Porogen}$, with $\theta_{S,Porogen}$ being the temperature at which the porogen dissolves in the solvent. By increasing $\theta_A$, the rate of dissolution of the porogen is increased, hence, time for washing out can be lowered. Depending on the requirements of the substances involved, $\theta_A$ can be kept as low as possible, whereby the lower limit is $\theta_{S,Porogen}$.

In order to adopt the process to different porogens, the procedure of washing out at least one porogen can be carried out in at least two stages. In particular, the temperature during one stage of washing out the first porogen can be lower than the temperature during a further stage of washing out the second porogen. Advantageously, temperature control can be carried out in such a way as to minimise energy consumption and thermal stress. For example, in a first step a temperature of 25° C. can be chosen, and in a subsequent step a temperature of 50° C. can be applied.

In order to ensure a substantially complete removal of porogen from the bone substitution material, the duration for washing out the at least one porogen can be of the order of a few hours.

The invention further provides a profiled body, in particular being producable using a method as described above, comprising a skeleton substance and having a porous structure with pores being interconnected with each other.

The profiled body provides a bone substitution material which has a high mechanical stability due to its skeleton. Because the invention enables choosing of the skeleton substance, a long-term in-vivo biocompatibility can easily be realised as well as a biodegradable bone substitution material. Due to the special porous structure, a bone substitution material is provided which can be used for guided bone healing.

It is further possible to produce a profiled body comprising a resorbable biomaterial, allowing release of controlled amounts of an active ingredient. In particular, no second surgical procedure is necessary to remove the bone substitution material. In addition, the bone substitution material can be made available in unlimited amounts.

The size and the external form of the profiled body can be freely adjusted to the given requirements. For example, the bone substitution material can be provided in blocks out of which a bone graft or implant to be used inside a patient's body is prepared. However, it is also possible to provide pieces made of the bone substitution material which are suitable to be directly used as bone grafts or implants.

In particular, the porous structure can comprise chamber-like pores and elongated pores, wherein the chamber-like pores are at least partially interconnected with each other by the elongated pores.

The term "chamber-like" refers to a volumetric design resulting from particles used as a porogen. That means, dimensions do not differ substantially in all three directions in space.

The structure provides the advantage of pores being accessible for osteoblasts and, at the same time, mass transfer is facilitated due to the elongated pores providing channels allowing for convective transport besides diffusion.

The elongated pores can have a cross-section perpendicular to their longitudinal axis having a diameter in the range of 150 μm to 200 μm, typically 170 μm. Pores with a particular diameter and, thus, connectivity are important because the presence of a pore size of at least 150 μm is an essential requirement for osteoconduction.

The chamber-like pores can have a mean diameter in the range of 250 μm to 400 μm, providing sufficient space for ingrowing osteoblasts.

The porosity of the bone substitution material can be in the range of $0.15 \leq \epsilon \leq 0.5$. The porosity $\epsilon$ is defined as ratio of the pore volume to the entire volume. In particular, the porosity can be increased or decreased, respectively, by adding more or less porogen. Depending on the requirements for a given application, the optimum porosity can be chosen for, on one hand, as much space for osteoblasts to ingrow as possible, and, on the other hand, as less hollow volume as necessary to ensure sufficient resistance against mechanical stress.

The skeleton substance of the profiled body can comprise a ceramic material. In general, all ceramics are suitable which are biocompatible. For example, $TiO_2$ and $Al_2O_3$ can be used as skeleton substance. In particular, the skeleton substance can comprise calcium phosphate which provides the advantage of being the chemical basis material of natural bone.

According to the invention, the skeleton substance can also comprise a polymer. A wide variety of polymers suitable allows advantageously for choosing a material substantially tailor-made for the requirements of the given application.

The compression strength of the profiled body according to the invention is equal to or above 20 MPa. Further, the elasticity module can be equal to or above 0.8 GPa. Therefore, a sufficient resistance against mechanical stress can be provided.

In order to provide further space for osteoblasts to ingrow, the profiled body can contain macropores having a mean diameter of at least 500 μm.

In addition, the profiled body can contain an active ingredient. Thus, in particular a drug-loaded implant can be provided that could reduce infections in bones. By changing the concentration of a solution of the active ingredient, for example an antibiotic solution, the amount of antibiotic within the biomaterial can be adjusted.

Further, the profiled body according to the invention has advantageous long-term release properties. At more than 7 days after starting releasing, the rate of releasing the active ingredient is at least twice the respective rate of releasing active gradient being coated, in particular dip-coated, at a profiled bodies surface. In particular, the ratio of active ingredient being released within the seventh to the tenth day after starting releasing to the total amount of active ingredient being released until the end of the tenth day is at least 2 wt.-%. Thus, the long-term release kinetics from such biodegradable implants can be improved by incorporation of the active ingredient into the implant, in contrary to conventional dip-coating techniques.

DESCRIPTION OF THE DRAWINGS

The invention is described hereinafter in detail by means of specific embodiments with reference to the accompanying drawings in which:

FIG. 4A: Spherical nanoparticles as obtained after precipitation. FIG. 4B: Agglomerates of the precipitated nanoparticles. FIG. 4C: Surface of a cold-isostatically pressed profiled body. FIG. 4D: Fracture surface of a cold-isostatically pressed material, FIG. 5 mechanical parameters of cold-isostatically pressed samples in comparison with other biominerals (bone and teeth) and biomaterials (selection from literature; references given below), FIG. 6 photograph of profiled body (left) and profiled body mechanically shaped with macropores (middle), schematic depiction of the shaped profiled body with examples for scaling, FIG. 7 Surface of cold-isostatically presse material after 72 h at pH 4.4 (resembling osteoclastic resorption) (Scanning electron microscopy, SEM). Left: low magnification, right: higher magnification.

EXAMPLE 1

Biomimetic carbonated apatite comparable in chemical composition and crystallinity to bone mineral was obtained by continuous fast precipitation in a special crystallisation device. Further information is given in the publiation "Continuous synthesis of amorphous carbonated apatite" of D. Tadic, F. Peters and M. Epple, Biomaterials (2002), pages 2553 to 2559, which is completely incorporated into this application by reference.

Briefly, aqueous solutions of $(NH_4)_2HPO_4$ and $(NH_4)_2CO_3$ with a molar ratio of $CO_3^{2-}$ to $PO_4^{3-}$ of 0.5:1 were continuously mixed under nitrogen atmosphere at 37° C. with an aqueous solution of $Ca(NO_3)_2$ to result in a $Ca^{2+}$ to $PO_4^{3-}$ molar ratio of 1.67:1 after mixing. Both solutions were adjusted previously to pH 10 with ammonia solution.

The obtained powder was immediately filtered to avoid crystal growth and dried at 70° C. All solutions were prepared with compounds of p.a. quality from Merck KGaA (Darmstadt, Germany).

The precipitated and dried calcium phosphate powder was analysed by X-ray diffraction (XRD; Bruker AXS D8 Advance; Cu Kα), infrared spectroscopy (IR; KBr; Perkin-Elmer 1720×), thermogravimetric analysis (TGA; TG/DTA-S II, Seiko Instruments Exstar 6000, 25-1000° C.; 10 K min$^{-1}$) and scanning electron microscopy (SEM; LEO 1530; gold-sputtered samples).

Elemental analysis of the samples gave a calcium content of 34.7 wt.-% (by atomic absorption spectroscopy), a phosphate content of 51.6 wt.-% (by photometry), a carbonate content of 4 to 5 wt.-% (by TGA; 400-1000° C.) and a water content of 7 to 8 wt.-% (by TGA; 100-400° C.). This corresponds to a molar Ca/P ratio of 1.59:1.

The dried carbonate apatite powders were ball-milled and sieved to particles having a mean diameter in the range of 250 to 400 μm particle size before processing. Compact ceramic bodies of variable shape were prepared by cold isostatic pressing at a pressure of 4000 bar in a Dieffenbacher Isostat press at room temperature of about 25° C.

Mechanical parameters were determined in an electromechanical testing machine (Schenck Trebel RM 100) (100 kN) with 0.5 mm min$^{-1}$ on samples with cylindrical shape of different size according to DIN EN 658-2. For each geometry, three objects were investigated and the results were averaged.

Figure 1:
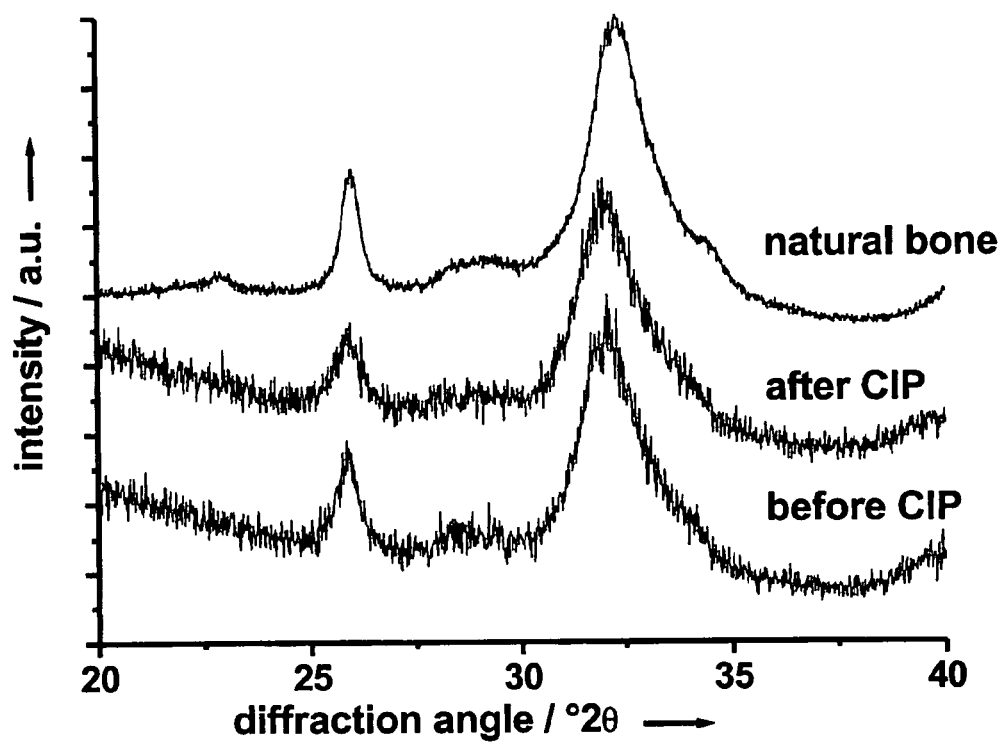
FIG. 1 X-ray powder diffractograms of natural bone and synthetic carbonated apatite before and after cold-isostatic pressing (CIP), FIG. 2 Infrared spectra of natural bone and synthedic bone mineral (carbonated apatite) before and after cold-isostatic pressing (CIP), FIG. 3 photograph of different profiled bodies of bone mineral-like calcium phosphate, prepared by cold-isostatic pressing, FIG. 4 Scanning electron micrographs of synthetic bone mineral.

FIG. 1 shows X-ray diffraction patterns of carbonated apatite (4 to 5 wt.-% carbonate content) before and after cold isostatic pressing in comparison with natural human bone. The diffractogram shows two very broad peaks at 26°2Θ and 31 to 34°2Θ that are typical for a poorly crystalline (nanocrystalline) apatite.

Figure 2:
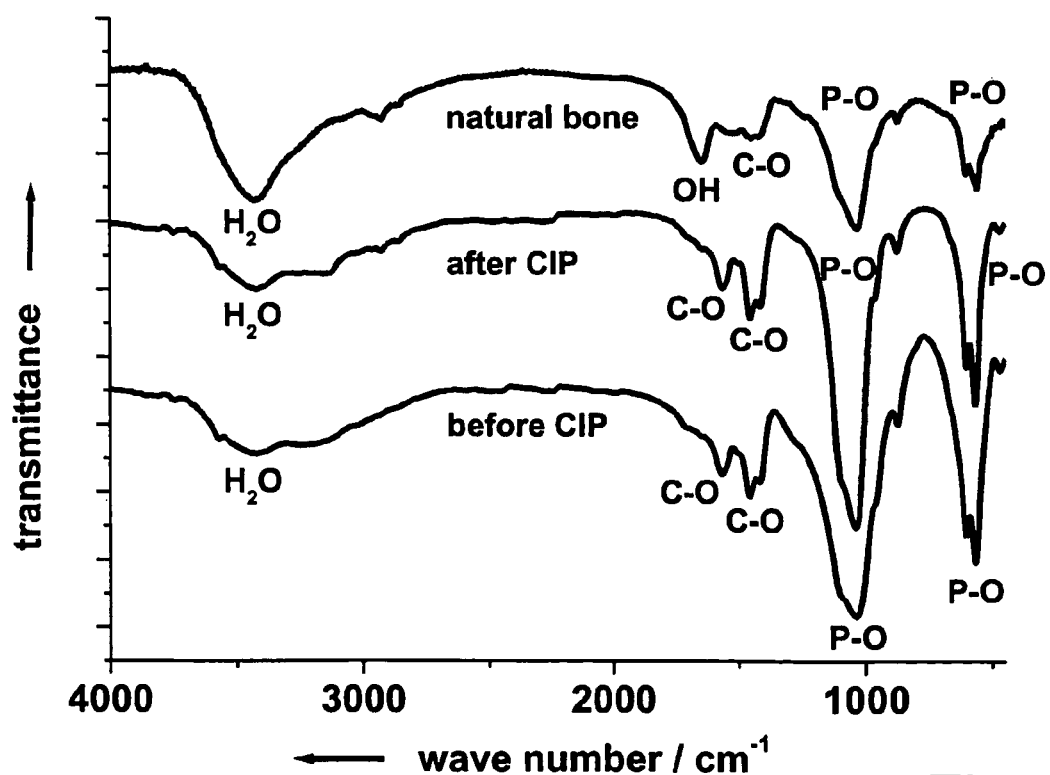
Figure 3:
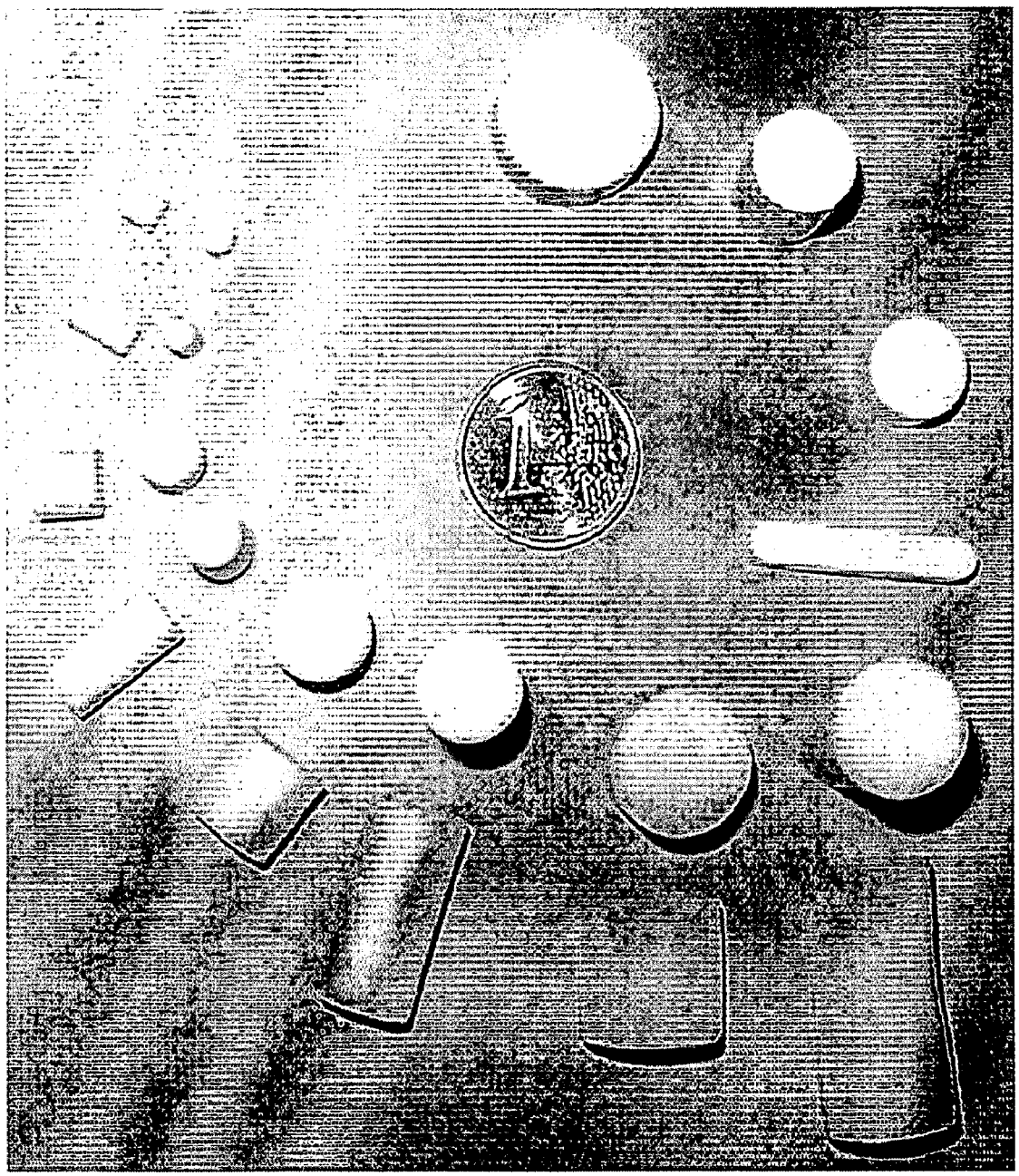

Cold isostatic pressing does not influence the crystal structure of the obtained carbonated apatite. This is supported by IR and TGA experiments before and after pressing that showed no change in the composition. In particular, the presence of carbonate is still evident from the IR absorption bands at 870, 1420, 1480, and 1540 cm$^{-1}$, (FIG. 2). Typical objects of different size and shape prepared by cold isostatic pressing are shown in FIG. 3.

After precipitation from solution, the material consists of almost uniform spheres with a diameter of about 20 to 40 nm (FIG. 4a). These are agglomerated to larger particles of irregular shape in the μm size range (FIG. 4b). After cold isostatic pressing, macroscopic objects are obtained that consist of the "fused" primary particles in unchanged geometry (FIGS. 4c and 4d). Again, we conclude that the nanocrystalline structure is not changed by the shaping process, that means that bone mineral-like material is still present.

Preliminary attempts to prepare macroscopic objects by uniaxial hot pressing (4 kbar, 240° C.) showed that the mechanical stability of such objects was limited due to insufficient compaction (FIG. 5). In addition, the objects were rather brittle, particularly at the edges. This was decisively improved by the cold isostatic pressing technique. For cylinders of different diameters and heights, obtained Young's moduli from 0.8 to 2.2 GPa and compression strengths of 21.8 to 47.6 MPa were obtained (FIG. 5).

In FIG. 5, mechanical parameters of cold-isostatically pressed samples in comparison with other biominerals (bone and teeth) and biomaterials are shown. The data of selected biomaterials have been taken from literature with the numbers referring to the following publications:
1) N. Verdonschot, C. T. H. van Hal, B. W. Schreurs, P. Buma, R. Huiskes, T. J. J. H. Sloof: Time-dependent mechanical properties of HA/TCP particles in relation to morsellised bone grafts for use in impaction grafting. J. Biomed. Mat. Res. Appl. Biomater. (2001), pages 599 to 604,
2) P. K. Zysset, X. E. Guo, C. E. Hoffler, K. E. Moore, S. A. Goldstein: Elastic modulus and hardness of cortical and trabecular bone lamellae measured by nanoindentation in the human femur. J. Biomechanics (1999), pages 1005 to 1012,
3) M. Bohner: Physical and chemical aspects of calcium phosphates used in spinal surgery. Eur. Spine J. (2001), pages 114 to 121,
4) T. N. G. Chu, D. G. Orton, S. J. Hollister, S. E: Feinberg, J. W. Halloran: Mechanical and in vivo performance of hydroxyapatite implants with controlled architectures. Biomaterials (2002), pages 1283 to 1293,
5) J. C. Le Huec, T. Schaeverbeke, D. Clement, J. Faber, A. Le Rebeller: Influence of porosity on the mechanical resistance of hydroxyapatite ceramics under compressive stress. Biomaterials (1995), pages 113 to 118,
6) R. I. Martin, P. W. Brown: Mechanical properties of hydroxyapatite formed at physiological temperature. J. Mater. Sci. Mater. Med. (1995), pages 138 to 143,
7) L. M. Rodriguez-Lorenzo, M. Vallet-Regi, J. M. F. Ferreira, M. P. Ginebra, C. Aparicio, J. A. Planell: Hydroxyapatite ceramic bodies with tailored mechanical properties for different applications. J. Biomed. Mat. Res. (2002), pages 159 to 166.

It is evident that the mechanical strength has improved by a factor of about 5 to 10 by using cold isostatic pressing instead of uniaxial hot pressing. Moreover, this is also demonstrated by an overall improved mechanical stability towards manual scratching, torsion and bending, including the edges. Although compressive strength and Young's modulus of the natural biomaterials bone and teeth are not achieved, the values are within the range of other porous or compact calcium phosphate-based biomaterials (FIG. 5).

Even after cold isostatic pressing, the material retains some porosity. A density of 1.9 g cm$^{-3}$ was determined. This is about 60% of the theoretical density of pure hydroxyapatite (3.16 g cm$^{-3}$), therefore we can conclude that the microporosity is about 0.4.

FIG. 4c shows that these pores are in the size-range of nanometers. An immersion of cold isostatically pressed cylinders in water for 24 h resulted in an uptake of 0.15 ml water per gram of ceramic. The objects are perfectly stable upon immersion in water, that means there is no disintegration of the objects.

Figure 6:
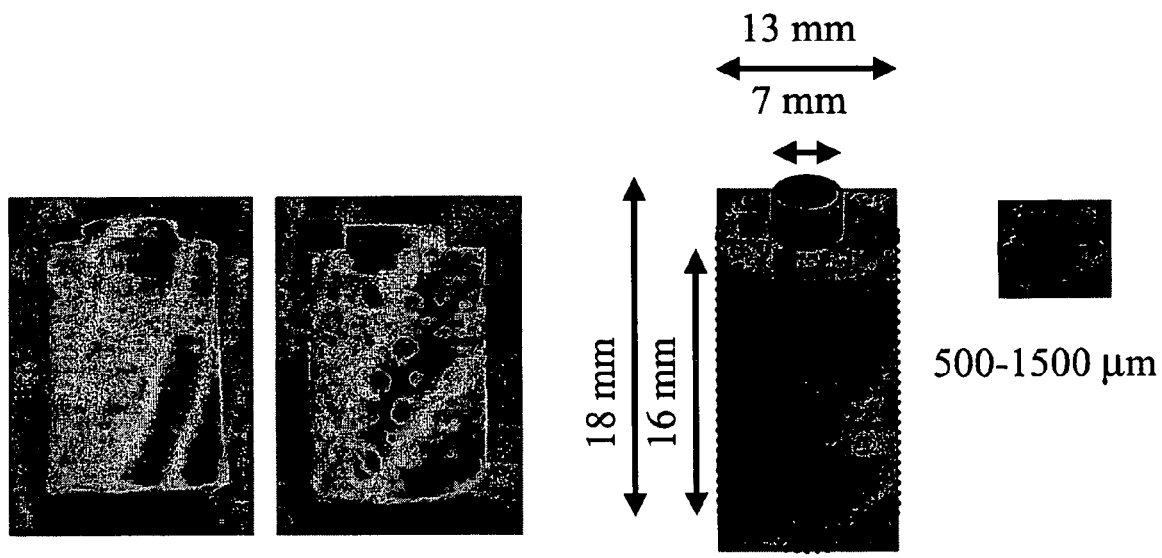

Mechanical shaping of these objects can be performed by cutting and drilling. For example, objects have been prepared with macropores of 500 μm, 1000 μm, and 1500 μm diameter, depending an the drill size used (FIG. 6).

Such objects are suitable as bone implants as osteoblasts are able to enter pores of this size. In vivo experiments of HAP implanted in rabbits showed a maximum in osteoconductivity at pore diameters of about 130 to 260 μm and 300 μm.

Under acidic conditions (pH 4.4), the synthesized carbonated apatites showed a much higher solubility than sintered calcium phosphate ceramics, like β-tricalcium phosphate (β-TCP) or highly crystalline sintered hydroxyapatite.

Figure 7:

The surface of cold-isostatically pressed objects of bone mineral-like apatite was investigated after the simulated osteoclastic resorption (after 72 h at pH 4.4). It shows "resorption pits" of about 2 μm diameter that incorporate submicrometer-sized needles (FIG. 7). Thus, macroscopic implants of this synthetic bone mineral should be resorbed within a reasonable time. A macroporous implant should also be degraded from within when bone cells have grown into the macroporous material (500 to 1500 μm).

EXAMPLE 2

Biomimetic carbonated apatite comparable in chemical composition and crystallinity to bone mineral was obtained by continuous fast precipitation in a crystallisation setup. Briefly, aqueous solutions of $(NH_4)_2HPO_4$ and $(NH_4)_2CO_3$ with a $CO_3^{2-}$ to $PO_4^{3-}$ molar ratio of 0.5:1 were continuously mixed under nitrogen atmosphere at 37 C with an aqueous solution of $Ca(NO_3)_2$ to result in a $Ca^{2+}$ to $PO_4^{3-}$ molar ratio of 1.67:1 alter mixing.

Both solutions were adjusted previously to pH 10 with ammonia solution beforehand. The obtained powder was immediately filtered off to avoid crystal growth and dried at 70° C.

The precipitated and dried calcium phosphate powder was analysed by X-ray diffraction (XRD; Bruker AXS D8 Advance; Cu Koa), infrared spectroscopy (IR; KBr; Perlon-Elmer 1720X), thermogravimetric analysis (TGA; TG/DTA-S II, Seiko Instruments Exstar 6000, 25-1000° C.; 10 K min$^{-1}$) and Scanning electron microscopy (SEM; LEO 1530; gold-sputtered samples).

Elemental analysis of the samples gave a calcium content of 34.7 wt.-% (by atomic absorption spectroscopy), a phosphate content of 51.6 wt.-% (by photometry), a carbonate content of 4 to 5 wt.-% (by TGA; 400-1000° C.) and a water content of 7 to 8 wt.-% (by TGA; 100-400° C.). This corresponds to a molar Ca/P ratio of 1.59:1.

The calcium phosphate powder was ball-milled and sieved to particles having a mean diameter in the range of 250 to 400 μm. The powder was thoroughly mixed with polyvinylalcohol fibres having a diameter of approximately 170 μm and a length of about 5 to 10 mm, and with NaCl crystals of a mean diameters of about 250 to 400 μm.

This mixture was cold-isostatically pressed at 4000 bar with a Dieffenbacher Isostat press at room temperature of approximately 25° C. Macroscopic objects were prepared in the size-range of centimetres. After pressing, both NaCl and PVA were removed by extraction in cold water having a temperature of approximately 20° C., followed by extraction in warm water having a temperature of approximately 50° C. for about 12 h each.

Synchrotron radiation based microtomography (μ-CT) was performed at beamline BW2 of HASYLAB at DESY using monochromatic X-rays. Images with and without the sample at different sample rotations equally stepped between 0 and π were recorded by the 2-dimensional X-ray detector. The 3-dimensional data set was calculated using the standard reconstruction technique of backprojection of filtered projections. The parameters for the measurement were as follows: photon energy 22 keV, number of projections 720, pixel size 3.5 μm. The reconstructed data set comprised 1536·1536·1024 voxel within a volume of 5.4·5.4·3.6 mm$^3$.

All compounds except for PVA were of p.a. quality from Merck KGaA (Darmstadt, Germany). PVA fibres (type SWN4; fibre dissolution temperature in water approx. 40° C. according to the manufacturer) were obtained from Kuraray Europe GmbH (Dusseldorf, Germany).

Figure 8:
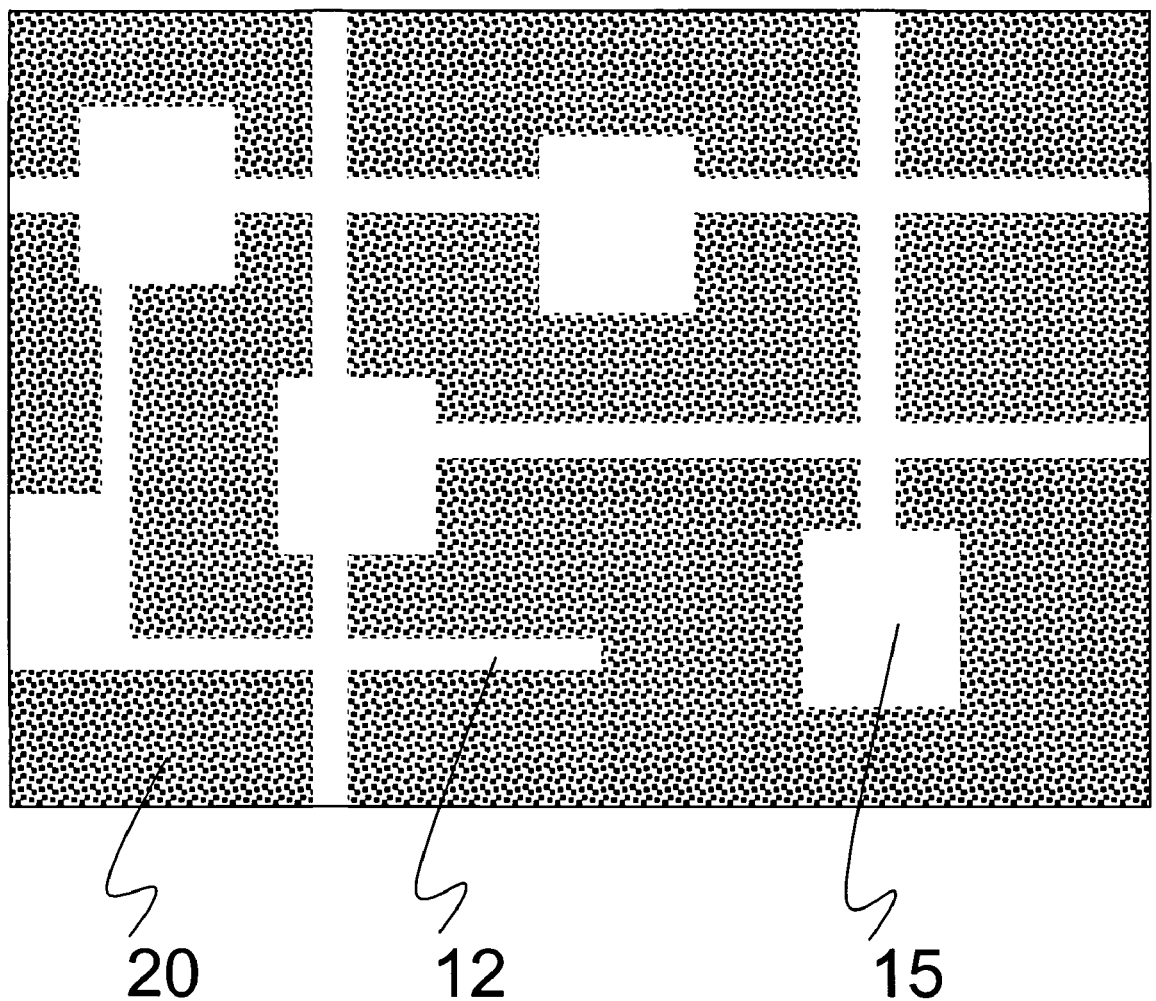
FIG. 8 a schematic representation view of a cross section of a profiled body according to the invention, FIG. 9 scanning electron micrographs of objects of carbonated apatite with interconnecting pores.

In FIG. 8, the porous structure 10 obtained by the method of the invention is generally depicted. In the skeleton substance 20, chamber-like pores 15 are formed by the salt crystals, and polymer fibres form elongated pores 12 acting as bridging channels between the chamber-like pores 15.

Figure 9:
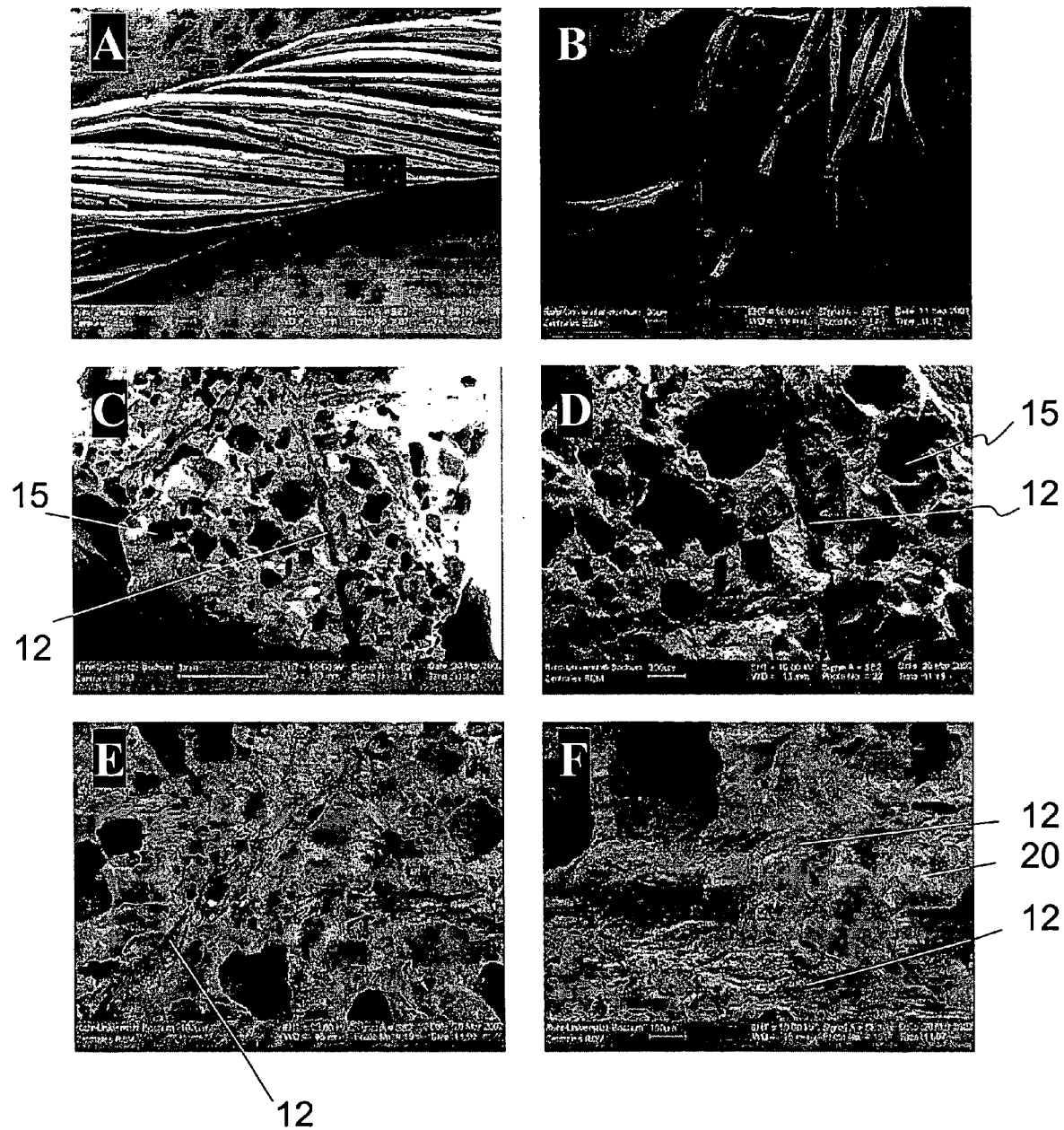
FIG. 9A: A PVA fibre that is itself spun from fibres of smaller diameter.
FIG. 9B: Fracture surface of a cold-isostatically pressed object containing NaCl and PVA as porogens before the extraction.
FIGS. 9C and 9D: Fracture surface of a cold-isostatically pressed object after the extraction of the porogens.
FIGS. 9E and 9F: Fracture surface of a cold-isostatically pressed object after the extraction of the porogens at a higher magnification, FIG. 10 Synchrotron computer microtomography of objects of carbonated apatite with interconnecting pores, FIG. 11 scanning electron micrographs (top) and synchrotron computer microtomography (bottom) of a composite consisting of calcium phosphate, NaCl and PVA, FIG. 12 a schematic representation of two methods to load a profiled body with an active ingredient by dip-coating (left) and co-precipitation (right), FIG. 13 infrared spectra of the material with and without the model active ingredient Gentamicin and of pure Gentamicin, FIG. 14 X-ray powder diffractogram of co-precipitated carbonated apatite with and without Gentamicin (loading of the carbonated apatite by co-precipitation), FIG. 15 Release curves of Gentamicin from loaded profiled bodies over 10 days.

FIG. 9 shows the general principle of the method illustrated by pictures of respective fractured surfaces. In FIG. 9A, as example for a polymer fibre acting as a porogen, a PVA fibre is shown. The PVA fibre is itself spun from smaller fibres having diameters of about 15 μm, resulting in an entire diameter of about 170 μm. In FIG. 9B, a fracture surface of cold-isostatically pressed profiled body consisting of 100 g calcium phosphate, 20 g NaCl and about 1 g of PVA is shown in a stage prior to the extraction of the porogens by water. In FIGS. 9C and 9D, respective fracture surfaces of equivalent objects are shown after the extraction with water. Whereas in FIG. 9B the porogens, in particular the polymer fibers are clearly visible, the comparison with the structures illustrated in FIGS. 9B and 9C shows the resulting chamber-like pores 15 and elongated pores 12. In FIGS. 9E and 9F, pictures of fracture surfaces of profiled bodies made from calcium phosphate after the extraction of PVA-fibres with water are depicted at a higher magnification showing the distinct morphology of the fibres (compare FIG. 9A) in the elongated pores 12 built in the skeleton substance 20.

Figure 10:
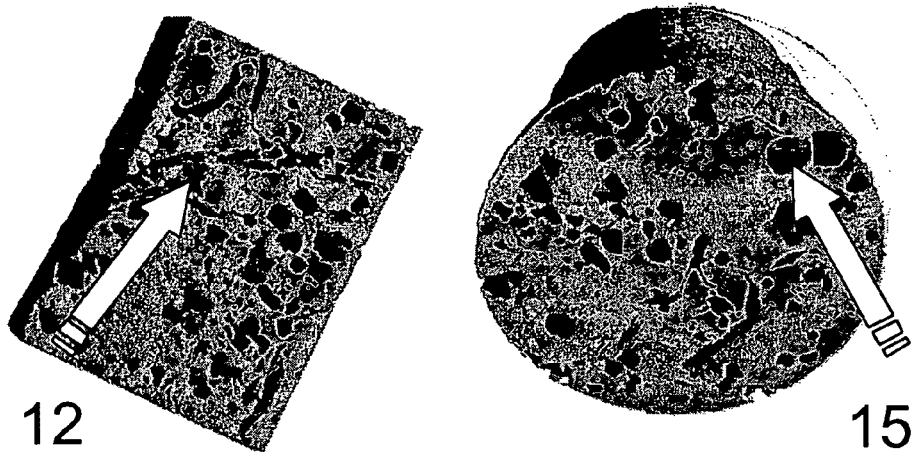

FIG. 10 shows two-dimensional cuts through three-dimensional objects which have been computed destruction-free from μ-CT data. The objects have a porosity of about 0.15. The interconnecting pores 12 resulting from the polymer fibres are clearly visible.

Figure 11:
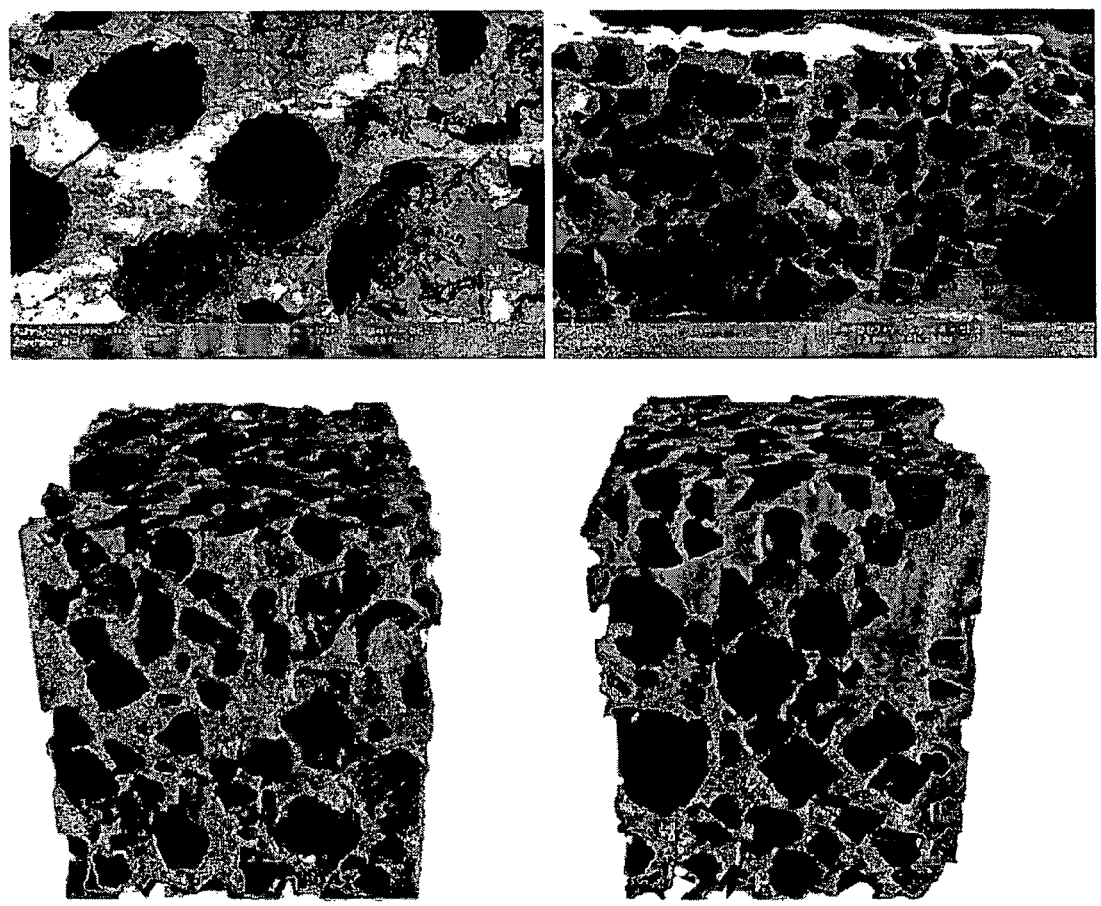

The porosity ϵ can be increased by adding more salt and/or more polymer. FIG. 11 shows objects with a porosity of about ϵ=0.47. The tube-like elongated pores 12 that are induced by the polymer are almost invisible because of the much higher fraction of chamber-like pores 15 from NaCl.

However, a sequence of two-dimensional cuts through the three-dimensional data set clearly shows the interconnecting porosity. If no polymer is used as porogen, it is much more difficult to extract the salt crystals which are not connected to the surface of the object. Therefore, by providing elongated pores interconnection of the chamber-like pores, the advantage of increasing the rate of mass transfer due to allowance of convection through the elongated pores acting as channels is achieved.

No problems with swelling of the polymer that might have led to cracks have been observed, that means the rate of dissolution is high enough. All porogens are quantitatively removed by the extraction with water as was demonstrated by X-ray diffraction and gravimetry. The nanocrystallinity of the calcium phosphate was neither changed by the cold-isostatic pressing nor by the extraction of the porogens, as demonstrated by X-ray diffractometry and infrared spectroscopy.

EXAMPLE 3

Biomimetic carbonated apatite comparable in chemical composition and crystallinity to bone mineral was obtained by continuous fast precipitation in a crystallisation setup. Briefly, aqueous solutions of $(NH_4)_2HPO_4$ and $(NH_4)_2CO_3$ with a $CO_3^{2-}$ to $PO_4^{3-}$ molar ratio of 0.5:1 were continuously mixed under nitrogen atmosphere at 37° C. with an aqueous solution of $Ca(NO_3)_2$ to result in a $Ca^{2+}$ to $PO_4^{3-}$ molar ratio of 1.67:1 after mixing. Both solutions were adjusted previously to pH 7.4 with ammonia solution (calcium nitrate) and nitric acid (ammonium phosphate/ammonium carbonate), respectively. The obtained powder was immediately filtered off to avoid crystal growth and dried at 70° C.

The precipitated and dried calcium phosphate powder was analysed by X-ray diffraction (XRD; Bruker AXS D8 Advance; Cu Kα), infrared spectroscopy (IR; KBr; Perkin-Elmer 1720X), thermogravimetric analysis (TGA; TG/DTA-S II, Seiko Instruments Exstar 6000, 25-1000° C.; 10 K min$^{-1}$) and scanning electron microscopy (SEM; LEO 1530; gold-sputtered samples).

Elemental analysis of the samples gave a calcium content of 34.7 wt.-% (by atomic absorption spectroscopy), a phosphate content of 51.6 wt.-% (by photometry), a carbonate content of 4 to 5 wt.-% (by TGA; 400 1000° C.) and a water content of 7 to 8 wt.-% (by TGA; 100-400° C.). This corresponds to a molar Ca/P ratio of 1.59:1.

The fine calcium phosphate powder was ball-milled and sieved to particles having a mean diameter in the range of 250 to 400 μm. Powders were cold-isostatically pressed at 4000 bar with a Dieffenbacher Isostat press at room temperature of approximately 25° C. Cylinders of 4.5 mm height and 4.5 mm diameter were prepared having a weight of about 110 to 130 mg each.

The elution of the specimens was performed in phosphate buffer (pH 7.4) as follows: Three cylinders of every formulation were immersed in 5 ml solution each. The solution contained the antibiotic Gentamicin as a model substance for an active ingredient. After 8 h, 1 d, 2 d, 3 d, 4 d, 7 d, and 10 d taken from the start of the experiment, the three cylinders were taken out of the solution, gently dried with paper tissue, and immersed into fresh solution. An amount of 1 ml from the 5 ml solution from the release experiment of each time step was taken for the activity test.

The concentration of released Gentamicin was determined by an in vitro experiment using the agar diffusion test method. Agar plates with 1 ml release solution were prepared with Medium 5 (Merck® nutrient solution), which were inoculated with *Bacillus subtilis*. After an incubation time of 24 h at 37° C., the inhibition zones on the agar plates were opto-electronically measured using the analytical system ISRA-BIOEYE®. Calibration curves were recorded to relate the size of the inhibition zone to the concentration of Gentamicin present in the 1 ml incubation solution.

The activity of the Gentamicin sulphate used was 67%. All results and concentrations given here refer to the active amount of Gentamicin sulphate, that means to 67% of the total weight of Gentamicin sulphate present. Gentamicin was present as sulphate and all denotations, concentrations etc. If the drug is called "Gentamicin", the term refers to Gentamicin sulphate.

Gentamicin was incorporated into macroscopic objects by three different methods:
1) Nanocrystalline calcium phosphate was cold-isostatically pressed to a cylinder. Each cylinder was dipped into 10 ml of an aqueous solution of 3.9 g Gentamicin for one hour. Subsequently, it was taken out of the solution and dried under air at 70° C.
2) 5 g of nanocrystalline calcium phosphate powder were thoroughly mixed with a solution prepared from 1 to 2 ml water with 0.17 g Gentamicin and subsequently dried under air at 70° C. The loaded powder was cold-isostatically pressed to cylinders. As a weight of 0.25 g of the drug (containing 0.17 g active Gentamicin) was added to 5 g calcium phosphate, the loading with active Gentamicin is about 0.17/5.25=3.2 wt.-%. Each cylinder of this series weighed 132 mg on average, therefore each cylinder contained about 4.2 mg active Gentamicin.
3) Three solutions were continuously mixed in the precipitation setup with equal volume flows: 0.09 M $Ca(NO_3)$, 0.054 M $(NH_4)_2HPO_4$+0.027 M $(NH_4)_2CO_3$, and 0.48 g $l^{-1}$ Gentamicin. Thereby, the drug is incorporated into the calcium phosphate particles which are continuously filtered off.

The powder is continuously washed with distilled water to remove adsorbed nitrate. This will also remove any adsorbed Gentamicin. The powder was dried under air at 70° C. and cold-isostatically pressed to cylinders.

Figure 12:
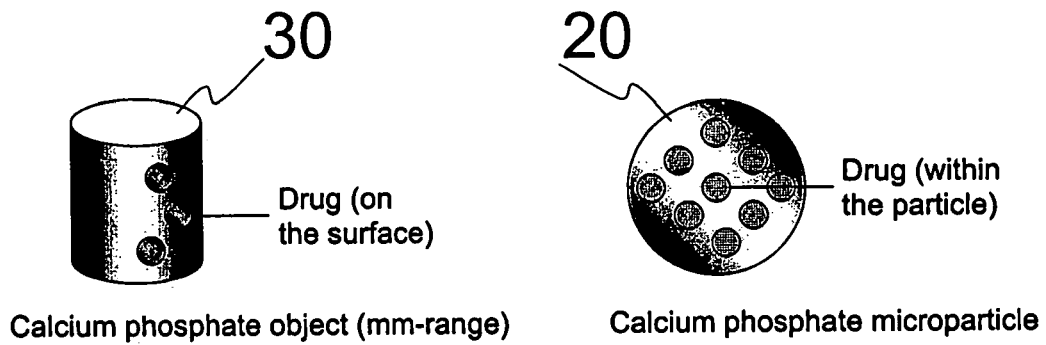

The methods lead to different loading forms as illustrated in FIG. 12. On the left hand side of FIG. 12, the result of dip-coating a profiled body into a solution is shown. A profiled body 30 comprises the active ingredient adsorbed at the surface. In addition, the active ingredient can also be adsorbed at the surface of internal pores. The adsorptive bond can be an electrostatic one, in particular, the bond is a non-covalent one. On the right hand side of FIG. 12, the result of co-precipitation of the skeleton substance 20 and the active ingredient is shown. Then, the profiled body 30 comprises the active ingredient included inside the particles of the skeleton substance 20.

Figure 13:
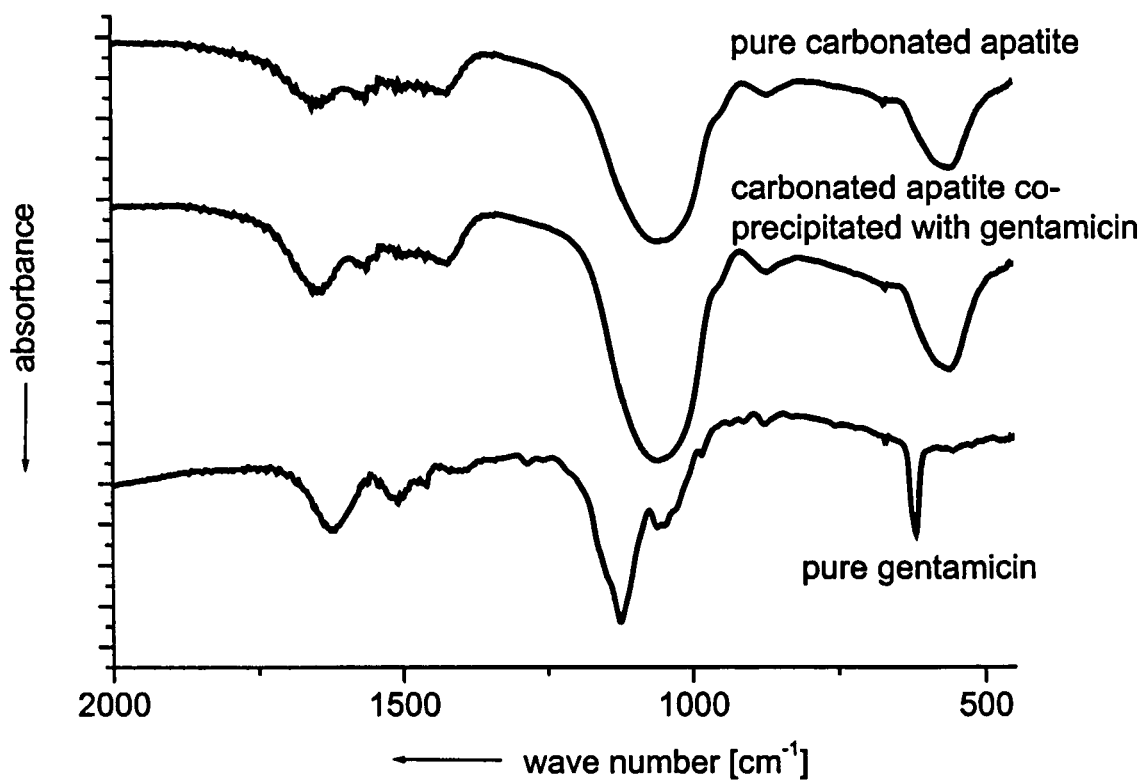

Dip-coating of cylinders leads to adsorption of the drug on the external surface and inside internal pores. The release kinetics are dominated to the adsorption-desorption equilibrium in solution, as shown in FIG. 13.

The co-precipitation leads to incorporation of the drug into the individual particles. The washing step ensures that adsorption an the external surface is kept to a minimum.

Impregnation of the powder with a drug solution, followed by shaping, leads to an intermediate kind of product where the drug is adsorbed an the surface of the individual particles. During cold-isostatic pressing, the particles are mechanically compacted and some drug is trapped into the interface of two adjoining particles. The release of the drug is therefore additionally restrained by diffusion out of the implant through pores of the profiled body.

Figure 14:
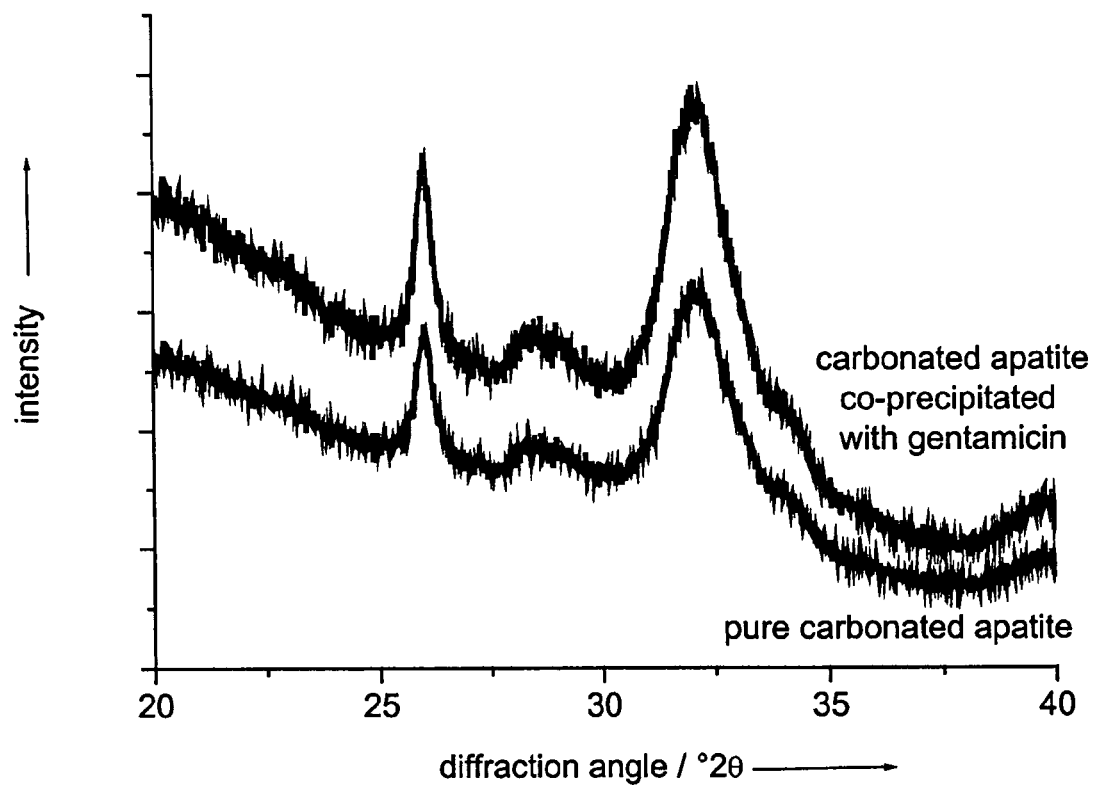
Figure 15:
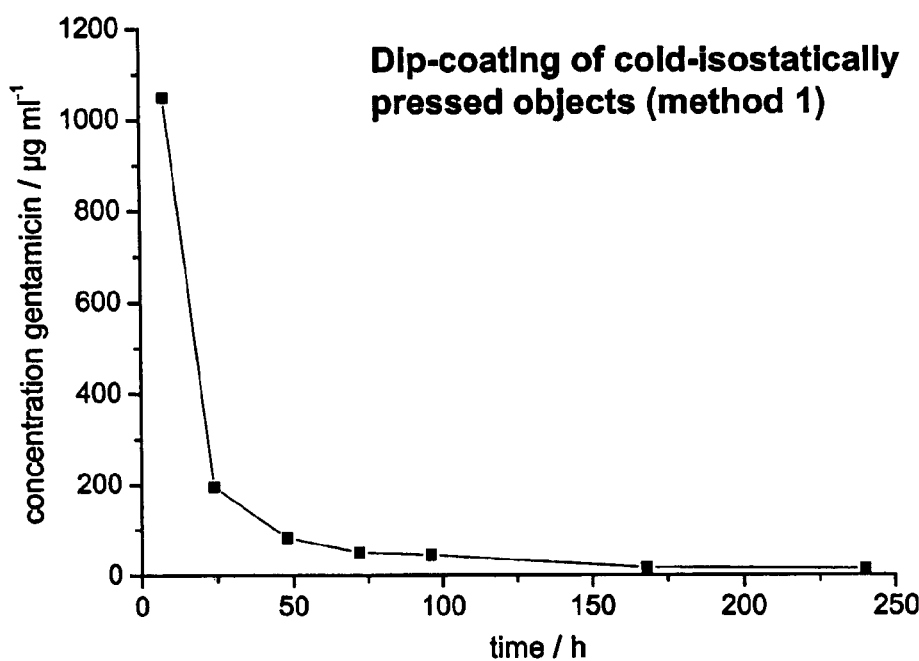
FIG. 15A: release curve of dip-coated profiled body.
FIG. 15B: release curve of profiled body made of impregnated powder.
FIG. 15C: release curve of profiled body made of powder co-precipitated with Gentamicin.
Figure 15:
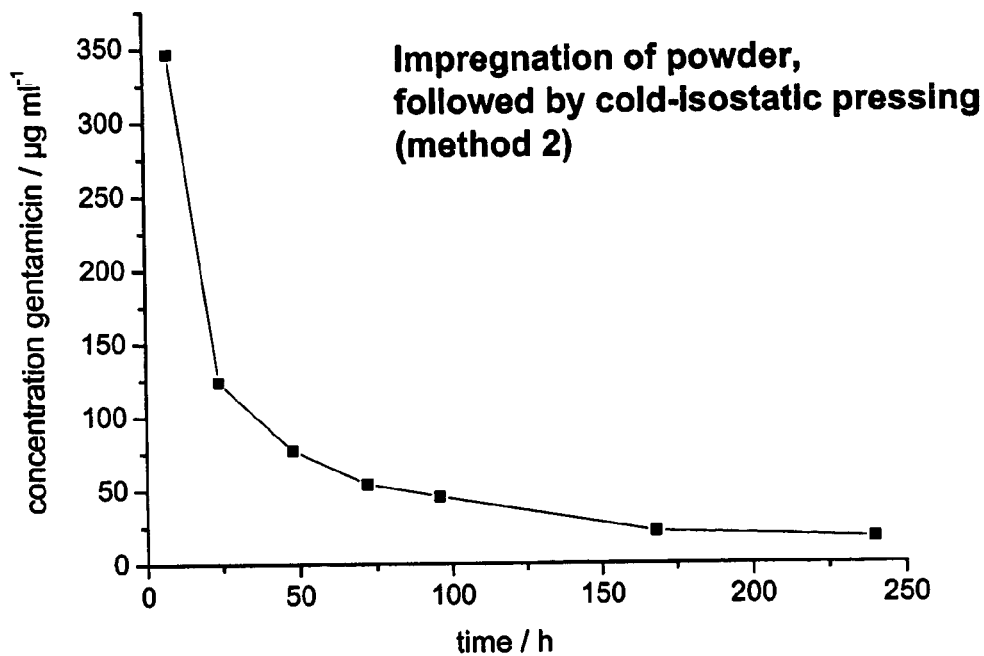
Figure 15:
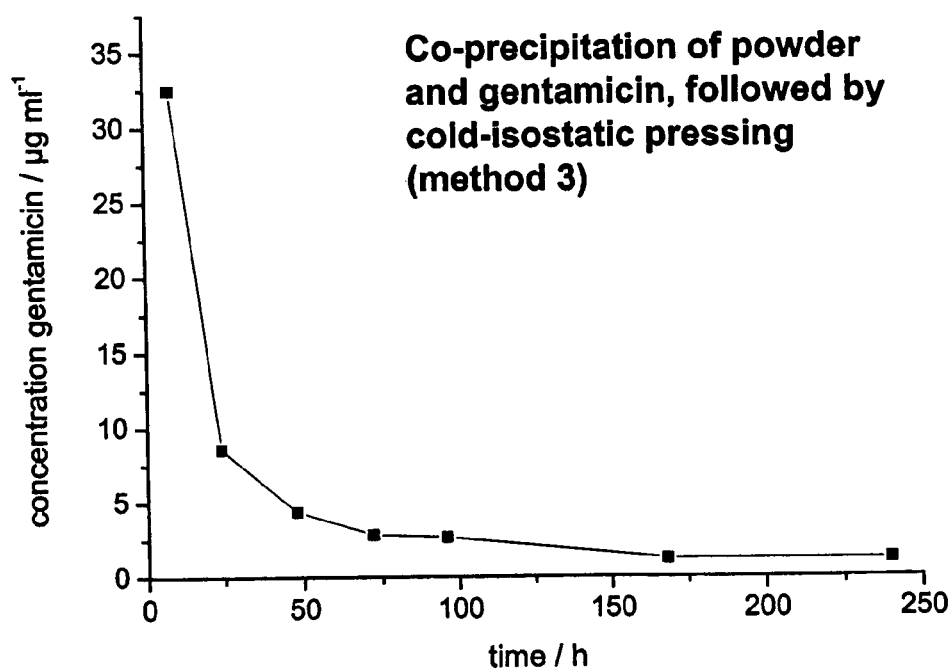

It is important to notice that Gentamicin does not lead to a change in the structural or chemical properties of the nanocrystalline calcium phosphate phase. FIGS. 14 and 15 demonstrate this with the infrared spectra and the X-ray powder diffractograms, recorded for co-precipitated samples. No substantial distinction can be made between the pure carbonated apatite and the drug-loaded carbonated apatite. This is also due to the comparatively low loading with the drug (see below). The compression strength of similar cylinders (but without Gentamicin) was determined to 25 to 28 MPa with an elasticity modulus of 0.8 to 1.1 GPa.

Further, the in vitro drug release of carbonate apatite objects from the different methods was studied. In FIGS. 15A to 15C, the concentration of Genatamicin in mg mL-1 is plotted against time in hours for samples resulting from the three methods of loading the profiled body with the drug.

Because the absolute loading is different in the three cases, the absolute amount of released Gentamicin is different. However, the shape of the curves is very similar, showing an initial burst up to 48 h, followed by a declining release rate up to 10 days.

The long-term release kinetics can be estimated by dividing the last point of the data curve (that is the release from day 7 to day 10) by the total amount of Gentamicin released from 0 to day 10 (the integral of the curve). For the dip-coating (method 1), this leads to 13.6/451=0.9%, for the impregnation (method 2) this leads to 17.2/685=2.5%, and for the co-precipitation (method 3) this leads to 1.2/53.4=2.2%. Thus, the long-term release is higher by a factor of about 2 to 2.5 with the incorporation methods than with the dip-coating method.

The fast release even with the methods 2 and 3 shows that the release kinetics are dominated by adsorption/desorption and also by diffusion out of the object. The degradation kinetics of calcium phosphate is negligible within 10 days, that means an "excavation mechanism" can be ruled out under which the drug release is controlled by the degradation of the surrounding calcium phosphate.

For method 2, the total load of the drug has been computed to 4.2 mg Gentamicin per cylinder. The total amount of detected Gentamicin (sum over all data points in FIG. 15B) is 685 μg $ml^{-1}$, corresponding to 3.425 mg Gentamicin in 5 ml solution. Thus, we have a release of about 3.425/4.2=82% during the first 10 days. It can be concluded that about one fifth of the drug is still present after 10 days.

From the shape of the curves presented in FIGS. 15A and 15C it may be assumed that after 10 days, most of the drug has been released from the dip-coated cylinder (method 1) whereas the co-precipitated material (method 3) still contains a considerable amount of the drug.

The three methods were also applied with a tenth of the respective concentration of Gentamicin. The results showed the same trend, of course with a factor of 10 in all concentrations.

The invention claimed is:

1. A method for producing a bone substitution material for implantation, comprising the steps of:
   providing a starting material comprising a mixture of at least a skeleton substance and a porogen composition, wherein the porogen composition comprises a water-soluble polymer fiber and a water-soluble particle;
   building up a skeleton from the starting material by cold-isostatic pressing to produce a profiled bone substitution material; and
   washing out the porogen composition prior to implantation to produce a porous structure, wherein the porous structure has chamber-like pores and elongated pores, wherein the chamber-like pores are at least partially interconnected with each other by the elongated pores to produce the bone substitution material.

2. The method according to claim 1, wherein said skeleton substance comprises a ceramic material.

3. The method according to claim 2, wherein the ceramic material comprises calcium phosphate.

4. The method according to claim 1, wherein said skeleton substance is conditioned to a powder comprising said water-soluble particle.

5. The method according to claim 1, wherein said water-soluble polymer fiber has a diameter in the range of 150 μm to 200 μm.

6. The method according to claim 1, wherein said water-soluble polymer fiber has a length in the range of 5 mm to 10 mm.

7. The method according to claim 1, wherein said water-soluble polymer fiber comprises poly-vinyl alcohol (PVA).

8. The method according to claim 1, wherein said water-soluble particle has a mean diameter in the range of 250 µm to 400 µm.

9. The method according to claim 1, wherein the porogen composition is embedded within the skeleton.

10. The method according to claim 1, wherein cold-isostatic pressing is carried out at a pressure in a range of 200 MPa to 600 MPa.

11. The method according to claim 1, wherein cold-isostatic pressing is carried out at a temperature range of 15° C. to 35° C.

12. The method according claim 1, wherein washing out the porogen composition is carried out using a solvent.

13. The method according to claim 12, wherein washing out the porogen composition is carried out at a temperature $\vartheta_A$ with $\vartheta_A \geqq \vartheta_{S, porogen}$, with $\vartheta_{S, porogen}$ being the temperature at which the porogen dissolves in the solvent.

14. The method according to claim 12, wherein the step of washing out the porogen composition has at least two stages.

15. The method according to claim 14, wherein the temperature during one stage of washing out the porogen composition is lower than the temperature during a further stage of washing out the porogen composition.

16. The method according to claim 12, wherein the duration for washing out the porogen composition is 12 hours.

17. The method according to claim 1, further comprising the step of adding at least one active ingredient to the bone substitution material prior to the washing out step.

18. The method according claim 17, wherein the at least one active ingredient is added to the profiled bone substitution material by dip-coating the profiled bone substitution material into a solution of the at least one active ingredient.

19. The method according to claim 17, wherein the at least one active ingredient is added by impregnating said skeleton substance with the at least one active ingredient.

20. The method according to claim 17, wherein the at least one active ingredient is added by co-precipitating said skeleton substance with the at least one active ingredient.

21. A method for producing a bone substitution material for implantation, comprising the steps of:
   providing a starting material comprising a mixture of at least a skeleton substance and a porogen composition, wherein the porogen composition comprises a water-soluble polymer fiber and a water-soluble particle;
   building up a skeleton from the starting material by cold-isostatic pressing to produce a profiled bone substitution material; and
   washing out the porogen composition prior to implantation to produce a porous structure, wherein the porous structure has chamber-like pores and elongated pores, wherein the chamber-like pores are at least partially interconnected with each other by the elongated pores to produce the bone substitution material,
   wherein the step of washing out the porogen composition has at least two stages, wherein the temperature during one stage of washing out the porogen composition is lower than the temperature during a further stage of washing out the porogen composition.

22. A method for producing a bone substitution material for implantation, comprising the steps of:
   providing a starting material comprising a mixture of at least a skeleton substance and a porogen composition, wherein the porogen composition comprises a water-soluble polymer fiber and a water-soluble particle;
   building up a skeleton from the starting material by cold-isostatic pressing to produce a profiled bone substitution material; and
   washing out the the porogen composition prior to implantation to produce a porous structure, wherein the porous structure has chamber-like pores and elongated pores, wherein the chamber-like pores are at least partially interconnected with each other by the elongated pores to produce the bone substitution material,
   wherein the duration for washing out the porogen composition is 12 hours.

* * * * *